(12) United States Patent
Yoon et al.

(10) Patent No.: US 8,685,700 B2
(45) Date of Patent: Apr. 1, 2014

(54) METHOD FOR ENHANCING PRODUCTION POLYHYDROXYALKANOIC ACID FROM MICROORGANISM STRAINS

(75) Inventors: Sung Chul Yoon, Jinju-si (KR); Ju Xu, Jinju-si (KR); Mun Hwan Choi, Jinju-si (KR)

(73) Assignee: Industry-Academic Cooperation Foundation Gyeongsang National University, Jinju-Si, Gyeongsangnam-Do (KR)

( * ) Notice: Subject to any disclaimer, the term of this patent is extended or adjusted under 35 U.S.C. 154(b) by 201 days.

(21) Appl. No.: 12/766,637

(22) Filed: Apr. 23, 2010

(65) Prior Publication Data

US 2011/0236936 A1 Sep. 29, 2011

(30) Foreign Application Priority Data

Jul. 27, 2009 (KR) .................. 10-2009-0068402

(51) Int. Cl.
| | |
|---|---|
| *C12P 7/62* | (2006.01) |
| *C12N 9/00* | (2006.01) |
| *C12N 1/20* | (2006.01) |
| *C12N 15/00* | (2006.01) |
| *C07H 21/04* | (2006.01) |

(52) U.S. Cl.
USPC ..... 435/252.3; 435/135; 435/183; 435/320.1; 536/23.2

(58) Field of Classification Search
None
See application file for complete search history.

(56) References Cited

PUBLICATIONS

Lee et al. Appl Environ Microbiol. Nov. 2001;67(11):4963-74.*
Dean et al. FEMS Microbiol Lett. May 7, 2002;210(2):277-83.*
"Recent Trends in Bioconvergence Technology", The Korean Society for Microbiology and Biotechnology, Jun. 25-26, 2009, Daejeon Convention Center, Korea, (2009).

* cited by examiner

*Primary Examiner* — Christian Fronda
(74) *Attorney, Agent, or Firm* — Kile Park Reed & Houtteman PLLC

(57) ABSTRACT

Provided is a method for enhancing the production of polyhydroxyalkanoic acid (PHA) from microorganism strains by disrupting a gene associated with the production of an exobiopolymer (EBP) in the *Pseudomonas* strain to redirect the carbon flux toward the production of the polyhydroxyalkanoic acid, thereby enhancing the production of the polyhydroxyalkanoic acid.

2 Claims, 8 Drawing Sheets

BM07
wild-type

BM07-59

BM07-59
(KT GalU)

I (LB Medium)

① ② ③

II (M1 Medium with 70 mM Fructose)

① ② ③

SEQUENCE LISTING

<160> NUMBER OF SEQ ID NOS: 5

<210> SEQ ID NO 1
<211> LENGTH: 28
<212> TYPE: DNA
<213> ORGANISM: Artificial Sequence

```
<220> FEATURE:
<223> OTHER INFORMATION: PCR primer for Pseudomonas galU gene
      amplification

<400> SEQUENCE: 1
cgcgaattct tccgtaccgt caacctgg                                              28

<210> SEQ ID NO 2
<211> LENGTH: 28
<212> TYPE: DNA
<213> ORGANISM: Artificial Sequence
<220> FEATURE:
<223> OTHER INFORMATION: PCR primer for Pseudomonas galU gene
      amplification

<400> SEQUENCE: 2
gctctagagg atcttgtgca gccagtga                                              28

<210> SEQ ID NO 3
<211> LENGTH: 22
<212> TYPE: DNA
<213> ORGANISM: Artificial Sequence
<220> FEATURE:
<223> OTHER INFORMATION: PCR primer for Pseudomonas galU gene
      amplification

<400> SEQUENCE: 3
ggtcatagct gtttcctgtc ag                                                    22

<210> SEQ ID NO 4
<211> LENGTH: 27
<212> TYPE: DNA
<213> ORGANISM: Artificial sequence
<220> FEATURE:
<223> OTHER INFORMATION: PCR primer for Pseudomonas galU gene
      amplification

<400> SEQUENCE: 4
atctcgagtt acagggcttc gtgcatg                                               27

<210> SEQ ID NO 5
<211> LENGTH: 28
<212> TYPE: DNA
<213> ORGANISM: Artificial Sequence
<220> FEATURE:
<223> OTHER INFORMATION: PCR primer for Pseudomonas galU gene
      amplification

<400> SEQUENCE: 5
cctctagatc accatagacg ttgttgcg                                              28
```

METHOD FOR ENHANCING PRODUCTION POLYHYDROXYALKANOIC ACID FROM MICROORGANISM STRAINS

CROSS-REFERENCE TO RELATED APPLICATION

This application claims the benefit of Korean Patent Application No. 2009-68402, filed Jul. 27, 2009, the disclosure of which is hereby incorporated herein by reference in its entirety.

BACKGROUND OF THE INVENTION

1. Field of the Invention

The present invention relates to a method for enhancing the production of polyhydroxyalkanoic acid (PHA), and more particularly, to a method for enhancing the production of polyhydroxyalkanoic acid (PHA) from microorganism strains by genetic manipulation of a wild-type microorganism strain.

2. Description of the Related Art

A variety of microorganisms are known to produce intracellular energy and carbon storage compounds known as polyhydroxyalkanoates (PHAs). PHAs have good thermoplastic properties, biodegradability, biocompatibility and other excellent traits which have attracted considerable academic and industrial interest. According to their side chain lengths, PHAs are divided into short-chain-length (SCL-) PHAs and medium-chain-length (MCL-) PHAs. The metabolic pathways used for bacterial MCL-PHA biosynthesis have been well known as two major routes found in *Pseudomonas*: (1) de novo fatty acid biosynthesis pathway, which produces (R)-3-hydroxyacyl-CoA precursors from non-related carbon sources, such as glucose and gluconate; and (2) fatty acid degradation by β-oxidation, which is the main metabolic route of fatty acids.

Many researchers produced PHAs using different types of techniques such as PHA synthesis-related gene insertion, a combination of different precursor carbon sources, multistep cultures, and the pathway routing by inhibitors. Although genes and their products directly related to MCL-PHA biosynthesis have been studied, little is known about the roles of other genes and gene products that may be indirectly involved in the PHA synthesis.

Extracellular polymeric substances (EPS) can be produced by various bacteria and perform important functions for the secreting organisms, including cell attachment or locomotion, protection from desiccation, resistance to toxins, and enhancement of their ability to sequester nutrients. According to its relative proximity to the cell surface, the EPS occur in two forms: (1) as capsular EPS, which is tightly linked to the cell surface via a covalent or noncovalent association; and (2) as slime EPS, which is loosely bound to the cell surface. The EPS is mainly composed of polysaccharides, proteins, lipids, a small amount of hexane, and other biopolymers. The composition and location of the PHA depend on several metabolic processes such as changes in growth phase, cell breakage due to cell death, active secretion, release of cell surface macromolecules (outer membrane proteins and lipopolysaccharides), and interaction with the environment. EPS biosynthesis and composition vary from one bacterial species to another and have been shown to be controlled by several environmental factors such as growth phase, growth media, temperature, limitation of oxygen and nitrogen, and cation deficiency. In recent years, interest in the exploitation of valuable EPS has been increasing for various applications in the food and pharmaceutical industries, heavy metal removal, and wastewater treatment, etc. EPS is also considered an abundant source of structurally diverse polysaccharides, some of which may possess unique properties for special applications. Polysaccharide biosynthesis requires an enzyme related to the synthesis of sugar nucleotide precursors as polysaccharide building blocks as well as a specific polysaccharide synthetase. Uridine triphosphate (UDP) glucose pyrophosphorylase (GalU) catalyzes the reversible formation of UDP-glucose and inorganic pyrophosphate (PPi) from UTP and glucose 1-phosphate. UDP-glucose not only functions as a precursor for polysaccharide biosynthesis but is also involved in the biosynthesis of several cell wall components. UDP-glucose is the substrate for the synthesis of UDP-glucuronic acid, and is also required for the interconversion of galactose and glucose by the Leloir pathway.

The inventors of the present invention have reported in a previous study that *Pseudomonas fluorescens* BM07 (hereinafter referred to as *P. fluorescen* BM07) secreted large amounts of exobiopolymer (EBP) when grown on fructose at 10° C. and played an important role in the bioremediation of heavy metals, especially in the cold season. The main components of the cold-induced EBP in BM07 are water-insoluble hydrophobic polypeptide(s) (up to 85%) and saccharides (8%). Carbohydrate analyses revealed glucose, glucosamine, and galactosamine as major components of the sugar units in the EBP. The isolated EBP exhibited an endothermic transition with an enthalpy of 84 J/g at 192° C. as well as a sharp X-ray diffraction pattern, suggesting a probable uniquely structured organization around cells.

The inventors of the present invention propose the production and characterization of *P. fluorescens* BM07 transposon mutants, which are disrupted in EBP formation but increase PHA accumulation compared with the wild type.

SUMMARY OF THE INVENTION

The present invention is directed to a method for enhancing the production of polyhydroxyalkanoic acid (PHA) from microorganism strains by disrupting a gene associated with the production of an exobiopolymer (EBP) in the *Pseudomonas* strain to redirect the carbon flux toward the production of the polyhydroxyalkanoic acid, thereby enhancing the production of the polyhydroxyalkanoic acid.

Moreover, the present invention is directed to a mutant of a *Pseudomonas* strain, the mutant being produced by disrupting a gene associated with the production of an exobiopolymer in the *Pseudomonas* strain.

In one aspect, the present invention provides a method for producing a polyhydroxyalkanoic acid (PHA) using a *Pseudomonas* strain, the method comprising disrupting a gene associated with the production of an exobiopolymer (EBP) in the *Pseudomonas* strain to redirect the carbon flux toward the production of the polyhydroxyalkanoic acid, thereby enhancing the production of the polyhydroxyalkanoic acid.

The *Pseudomonas* strain is not particularly limited but may include *Pseudomonas fluorescens*, and more preferably *Pseudomonas fluorescens* BM07 (Accession no.: KCTC 10005BP).

The gene associated with the production of the exobiopolymer (EBP) may include any gene associated with the production of the exobiopolymer (EBP), and preferably, galU.

In another aspect, the present invention provides a mutant produced by disrupting a gene associated with the production of an exobiopolymer in a *Pseudomonas* strain.

The *Pseudomonas* strain is not particularly limited but may include *Pseudomonas fluorescens*, and more preferably *Pseudomonas fluorescens* BM07 (Accession no.: KCTC 10005BP).

The gene associated with the production of the exobiopolymer (EBP) may include any gene associated with the production of the exobiopolymer (EBP), and preferably, galU.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1A:
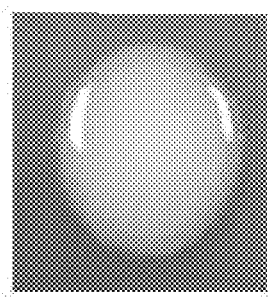
FIG. 1A shows the colony morphology of *P. fluorescens* BM07 wild type, BM07-59, and BM07-59 (KT GalU).
Figure 1A:
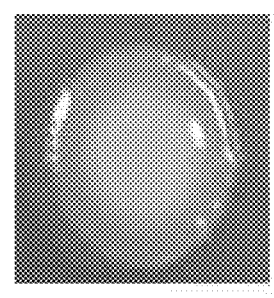
Figure 1A:
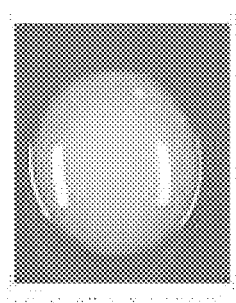

Hereinafter, the present invention will be described in detail with reference to Examples and the accompanying drawings. The following examples are merely illustrative and are not intended to limit the invention, the scope of which is defined by the appended claims.

EXAMPLES

Bacterial Strains, Medium and Cultivation Conditions

The bacterial strains, plasmids and oligonucleotides used in the present invention are listed in the following Table 1.

*Escherichia coli* strains and all its recombinants harboring different plasmids were cultivated at 37° C. in Luria-Bertani (LB) medium. *P. fluorescens* BM07 and its mutants were grown at 30° C. in LB media as inoculative medium and grown in 500 mL of M1 mineral salts medium (1.06 g (NH$_4$)$_2$SO$_4$, 2.3 g KH$_2$PO$_4$, 7.3 g Na$_2$HPO$_4$.12H$_2$O, 0.25 g MgSO$_4$.7H$_2$O, 0.3 g NaHCO$_3$, 0.1 g CaCl$_{2.2}$H$_2$O, 0.03 g ferric ammonium citrate, and 2 ml microelement solution) with shaking at 150 rpm. The microelement solution was produced by adding 0.556 g FeSO$_4$.7H$_2$O, 0.396 g MnCl$_2$.4H$_2$O, 0.034 g CuCl$_{2.2}$H$_2$O, 0.06 g H$_3$BO$_3$, 0.006 g NaMoO$_4$.2H$_2$O, 0.562 g CoSO$_4$.7H$_2$O, 0.058 g ZnSO$_4$.7H$_2$O, and 0.004 g NiCl$_2$.6H$_2$O to 200 ml of 0.5N hydrochloric acid. When required, antibiotics such as 100 µg/ml ampicillin, 20 µg/ml kanamycin, and 34 µg/ml chloramphenicol were added to the growth media.

TABLE 1

Bacterial strains, plasmids and oligonucleotides used in the Examples of the present invention

| Strains/ plasmids | Relevant characteristics | Sources of references |
|---|---|---|
| Strains | | |
| *E. coli* S17-1 | recA harboring the tra genes of plasmid RP4 in the chromosome, proA, thi-1 | Simon et al. (1983) |
| *P. fluoresens* BM07 | wild type, Isolated from activated sludge, medium-chain-length polyhydroxyalkanoates-producing strain | Lee et al. 2001 |
| BM07-ΔphaZ | Derivative of BM07, phaZ-, phaZ-lacZ | this study |
| BM07(pBBR-phaZ) | BM07 derivative containing pBBR-phaZ | this study |
| BM07-ΔphaZ(pBBR-phaZ) | BM07-ΔphaZ mutant derivative containing pBBR-phaZ | this study |
| Plasmids | | |
| pVIK112 | R6 K, promoterless lacZ, Km$^R$ | Kalogeraki and Winans (1997) |
| pXJZ | phaZ internal fragment in pVIK112 | this study |

TABLE 1-continued

Bacterial strains, plasmids and oligonucleotides
used in the Examples of the present invention

| Strains/ plasmids | Relevant characteristics | Sources of references |
|---|---|---|
| pBBR1MCS2 | $Cm^R$ broad host vector | Kovach et al. (1995) |
| pBBR-phaZ | pBBR1MCS2 derivative containing phaZ gene from P. fluorescens BM07 | this study |
| Oligonucleotides | | |
| 07Z-F | 5'-CGCGAATTCTTCCGTACCGTCAACCTGG-3' | SEQ ID NO: 1 |
| 07Z-R | 5'-GCTCTAGAGGATCTTGTGCAGCCAGTGA-3' | SEQ ID NO: 2 |
| pVIK-R | 5'-GGTCATAGCTGTTTCCTGTCAG-3' | SEQ ID NO: 3 |
| 07phaZ-F | 5'-ATCTCGAGTTACAGGGCTTCGTGCATG-3' | SEQ ID NO: 4 |
| 07phaZ-R | 5'-CCTCTAGATCACCATAGACGTTGTTGCG-3' | SEQ ID NO: 5 |

Genetic Techniques

Standard DNA manipulation techniques were used. Plasmid DNA was prepared using Miniprep extraction kit. Restriction enzymes and T4 DNA ligase were purchased from New England Biolabs. Polymerase chain reactions (PCR) using Taq DNA polymerase (Invitrogen) were performed according to the manufacturer's protocol. Oligonucleotide primers were purchased from Genotech (Korea). DNA was sequenced using BigDye terminator sequencing kit (Applied Biosystems) on an automated DNA Sequencer, model 310 (Perkin Elmer).

Screening for Mucoid-Deficient Mutants

Transposon mutants were generated by conjugating *P. fluorescens* BM07 with *E. coli* S17-1 carrying the mariner transposon vector pKGL3 as follows. Recipient (*P. fluorescens* BM07) and donor (*E. coli* 517-1: pKGL3) were grown separately in LB medium to late log phase ($A_{600}$ nm=0.6-0.8), and 5 mL of the recipient was added to 5 mL of the donor. Cells were pelleted at 5,000 rpm and 4° C. for 5 minutes, the medium was decanted and the cells were resuspended in 200 mL of LB medium. The entire 200 mL was spotted on an LB plate and incubated at 30° C. overnight. After incubation, the cells were scraped from the LB plate and resuspended in 1 mL LB medium, and 100 mL was subsequently plated on LB plates supplemented with kanamycin and ampicillin. Non-mucoid colonies were selected for further characterization.

Arbitrary PCR and Nucleotide Sequence Analysis

Arbitrary PCR was performed as described below to obtain short fragments of chromosomal DNA flanking transposon ends. The PCR products of the second round were sequenced with the transposon primer used in the second round, and the sequences were compared with the GenBank DNA sequence database using BLASTX program. The full sequence in the PCR products obtained from the arbitrary PCR was obtained by subcloning the transposon insertion flanking regions into pGEM-T Easy (Promega). To identify the galU gene, a fragment of this gene was obtained by the PCR using degenerate primers 07 galU-F1 and 07 galU-R2 prepared based on conserved regions of galU nucleotide sequences from several *Pseudomonas* spp. The accession number of BM07 galU in the GenBank database is FJ952543.

Complementation Experiment

To complement BM07-59 by the corresponding gene galU, the gene was amplified from *Pseudomonas putida* KT 2440 (KT2440 galU gene has identity and similarity of 92% and 97% to BM07 galU gene, respectively) as follows. The galU gene was amplified with the primers KT galU-F containing a restriction site of EcoRI and KT galU-R containing a restriction site of XbaI. The PCR product was digested with EcoRI and XbaI, followed by ligation with EcoRI/XbaI digested pBBR1MCS2 to produce pBBR-KTgalU. The thus produced construction pBBR-KTgalU was then introduced into the mutant BM07-59 for complementation.

Motility Assay

Mobility was evaluated using LB medium supplemented with 0.3% agar. First, *P. fluorescens* BM07 mutants and complement were incubated in LB medium containing 1.8% agar at 30° C. overnight. The bacteria from a single colony grown overnight on LB agar plates were inoculated with a sterile toothpick and the plates were kept at 30° C. for 48 hours. For each strain, the value of mobility was determined over a minimum of three independent measurements.

Lipopolysaccharide Analysis

*P. fluorescens* BM07 lipopolysaccharides (LPS) were obtained by proteinase K digestion of whole cells. Briefly, the cells in early stationary phase were harvested by centrifugation (at 10,000 rpm and 4° C. for 5 minutes). The pellets were suspended in phosphate-buffered saline (PBS) and the $OD_{600\ nm}$ was adjusted to 5. A 1-mL aliquot of the suspension was centrifuged for at 10,000 rpm and 41° C. for 5 minutes. The pellets were solubilized in 200 mL of lysing buffer containing 2% SDS, 4% 2-mercaptoethanol, 10% glycerol, 1M Tris (pH 6.8), and bromophenol blue. Lysates were heated at 100° C. for 10 minutes. A 3-μL aliquot of 20 $μL^{-1}$ proteinase K was added to each boiled lysate and incubated at 60° C. for 60 minutes. LPS samples were separated by sodium dodecyl sulfate polyacrylamide gel electrophoresis (SDS-PAGE) and the separated bands were visualized by silver staining. For composition analysis, LPS extraction and purification were carried out as described previously (Darveau & Hancock, 1983). Glycosyl composition analysis was performed at the Complex Carbohydrate Research Centre (University of Georgia, Athens, Ga.). The purified LPS samples were hydrolyzed using 1M methanolic-HCl at 80° C. for 14 hours. The released sugars were derivatized with Tri-Sil and the derivatized sample was analyzed by GC-MS using a Supelco EC-a fused silica capillary column.

PHA Analysis Using as Chromatograph

The cells were isolated by centrifugation (at 10,000 rpm for 10 minutes) of the cell suspension, washed with methanol and dried under vacuum at room temperature for 48 hours. Cell growth was determined by measuring dry cell weight (DCW). For the analysis of PHAs in cells, 15 mg of dried cells was reacted with a mixture containing 1 mL chloroform, 0.85 mL of methanol, and 0.15 mL concentrated sulfuric acid at 100° C. for 3 hours. The organic layer containing methyl esters of the PHA products was separated, dried over $Na_2SO_4$ and analyzed using a Hewlett-Packard HP5890 Series II gas chromatograph equipped with a HP-5 capillary column and a flame ionization detector. A typical GC run condition is as follows: initial temperature of 80° C. for 2 minutes; heating rate of 8° C./min; final temperature of 250° C. for 1.75 minutes; carrier (He) flow rate of 3 mL/min; injector temperature of 230° C.; and detector temperature of 280° C.

Next, the results according to the above-described Examples of the present invention will be described.
Identification of the EBP-Defective Mutants The inventors have found in a previous study that *P. fluorescens* BM07 strain produced an excess amount of exobiopolymer (EBP) (~1.4 g/L) in a limited M1 medium supplemented with 70 mM fructose at 10° C., whereas the cells grown at 30° C. secreted only a negligible amount of exobiopolymer. The cold-induced EBP produced by *P. fluorescens* BM07 was suggested to play important roles in removing heavy metals. However, the molecular basis for the regulation of the cold-induced EBP production is not yet known. To study the regulation of the EBP production, mutants defective in EBP production were screened from a transposon insertion mutant library of *P. fluorescens* BM07. Eighty-five mutants showing the phenotype of slime deficiency, determined from the change of colony morphology, were isolated among approximately 15,000 random transposon insertion mutants on LB agar. Each of the 85 mutants was assessed for exobiopolymer and lipopolysaccharide synthesis. Eight mutants completely abolished EBP production and O-antigen lipopolysaccharide synthesis and showed increased PHA accumulation compared with the wild type.

Figure 1B:
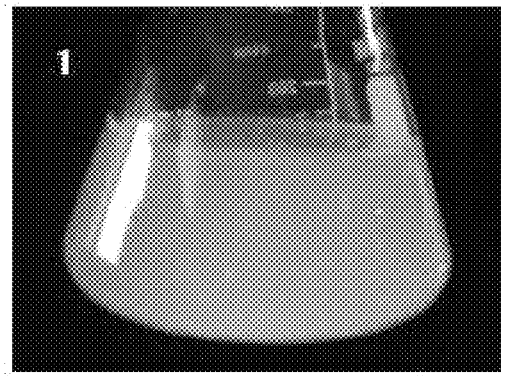
FIG. 1B shows supernatants collected by centrifuging culture media of BM07 wild type (1), BM07-59 (2), and BM07-59 (KT GalU) (3), which were grown in M1 medium with 70 mM fructose at 10° C. for 7 days.
Figure 1B:
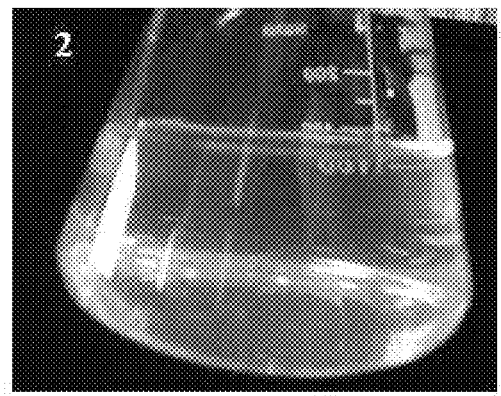
Figure 1B:
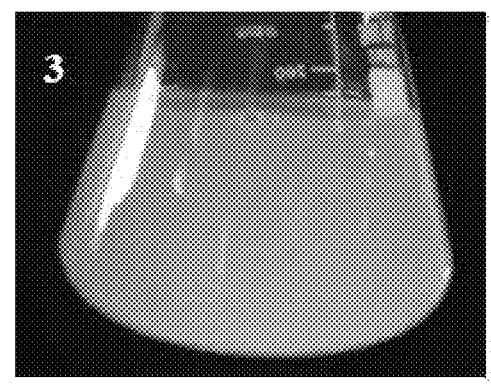

One of the eight mutants, which showed the greatest increase in the PHA accumulation, was chosen and named BM07-59. The colony morphology of BM07-59 was distinct from that of the wild type. As shown in FIG. 1A, the mutant colony exhibited an alteration in slime production and appeared less glossy than the parent strain. As shown in FIG. 1B, the cultivation of BM07-59 in M1 minimal medium with 70 mM fructose at 10° C. did not lead to the production of exobiopolymer. In FIG. 1B, after centrifugation, the supernatant from BM07-59 was clear, whereas the supernatant from BM07 wild type was very turbid due to the presence of water-insoluble colloidal EBP particles in the supernatant.
Identification of the Gene Disrupted in EBP-Defective Mutant (BM07-59)

Arbitrary PCR was used to determine the precise location of the transposon insertion. According to the following table 2, the sequencing of the region in BM07-59 flanked by the transposon revealed that the transposon was inserted into the gene that has high similarity to galU from *Pseudomonas fluorescens* Pf-5, *Pseudomonas fluorescens* Pf0-1, *Pseudomonas putida* KT2440, and *Pseudomonas aruginosa* PAO1. As shown in Table 2, the full galU gene obtained from BM07 was found to have a sequence encoding a protein exhibiting a high sequence homology with UDP-glucose pyrophosphorylase (GalU).

TABLE 2

| Mutant | Insertion site | Similar protein/organism | Identity/Similarity (%) | E | Product | Accession No. |
|---|---|---|---|---|---|---|
| BM07-59 | 379-380 | galU/ *P. fluorescens* pf-5 | 99/99 | 8.00E−159 | UTP-glucose-1-phosphate uridylyltransferase | AAY92668.1 |
| | | galU1/ *P. fluorescens* Pf0-1 | 99/98 | 1.00E−157 | UDP-glucose pyrophosphorylase | ABA74670.1 |
| | | galU/ *P. putida* KT2440 | 92/97 | 2.00E−149 | UTP-glucose-1-phosphate uridylyltransferase | AAN69415.1 |
| | | GalU2/ *P. fluorescens* Pf0-1 | 81/91 | 9.00E−132 | UDP-glucose pyrophosphorylase | ABA75573.1 |

UDP-glucose pyrophosphorylase, which catalyzes the reversible formation of UDP-glucose and inorganic pyrophosphate (PPi) from UTP and glucose 1-phosphate, has been recognized as a pathogenic factor in several bacteria species including *Streptococcus pneumoniae, Pseudomonas aeruginosa*, and *Shigella flexneri*. UDP-glucose functions as sugar nucleotide precursor for polysaccharide biosynthesis and is a potential intracellular signal molecule which is also involved in the biosynthesis of several cell wall components. A relevant role for GalU in virulence has also been recognized in several bacterial species, as this enzyme is required for the synthesis of UDP-glucose, which is the main glucosyl donor in lipopolysaccharide and capsule biosynthesis.
Characterization of *P. Fluorescens* BM07 EBP-Defective Mutant (BM07-59)

Figure 2:
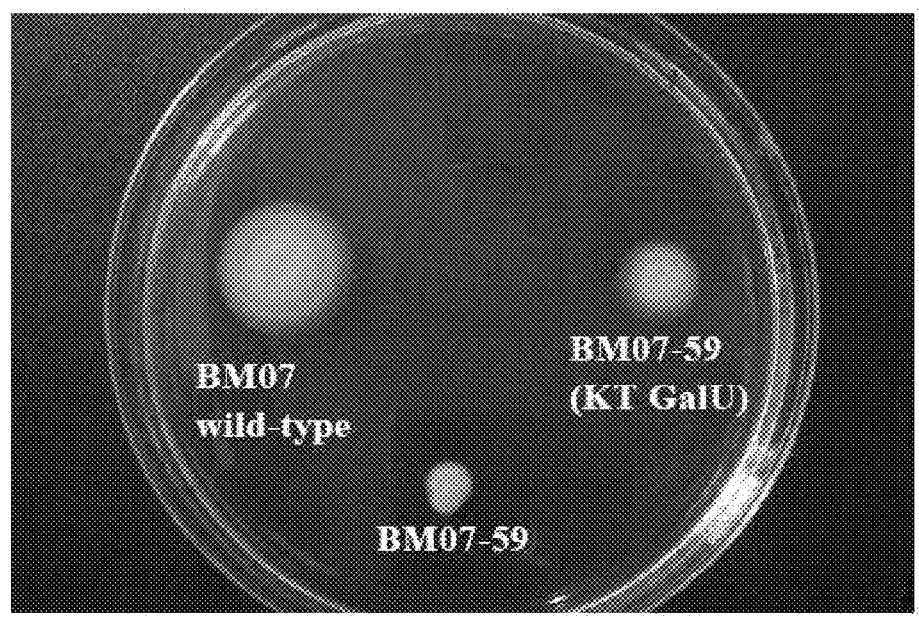
FIG. 2 shows the motility of BM07 wild type, BM07-59, and BM07-59 (KT GalU) inoculated on LB soft agar (0.3% agar).
Figure 3A:
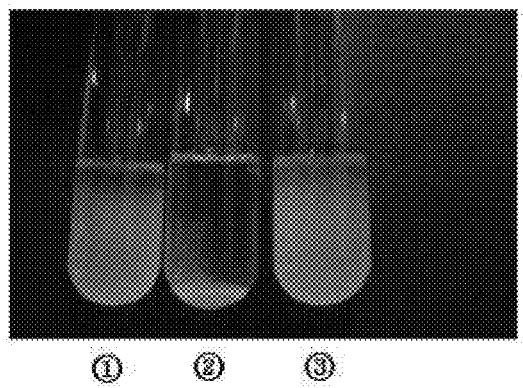
FIG. 3A shows autoagglutination phenotypes of *P. fluorescens* BM07 wild type (1), BM07-59 (2), and BM07-59 (KT GalU) (3), in which the strains were grown in LB medium (I) and M1 medium with 70 mM fructose (II) under agitation and then left unshaken for 3 hours.
Figure 3A:
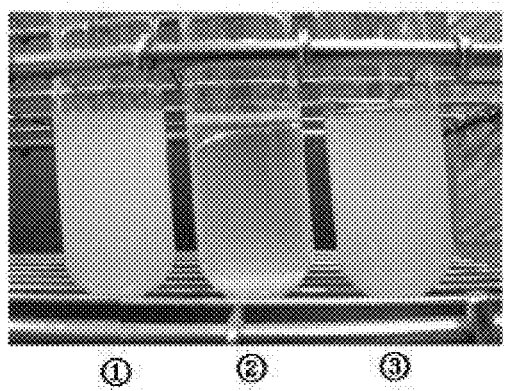
Figure 3B:
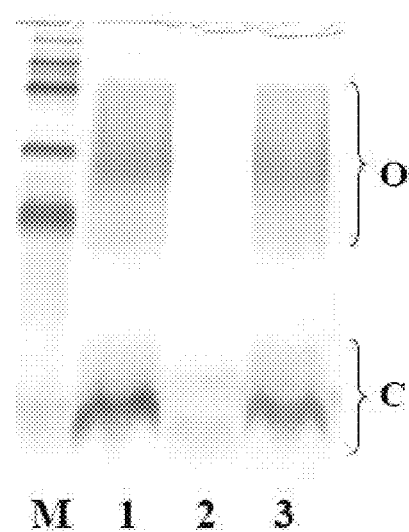
FIG. 3B shows lipopolysaccharides profiles on SDS-PAGE gel, in which periodic acid silver stained SDS-PAGE gel (15%) of proteinase K-treated SDS extracts of *P. fluorescens* BM07 wild type (lane 1), BM07-59 (lane 2), and BM07-59 (KT GalU) (lane 3), wherein M represents the marker, O represents the O-antigen lipopolysaccharides, and C, represents the lipopolysaccharide-core.

As shown in FIG. 2, when tested on LB medium containing 0.3% agar, the wild-type strain was able to swim, whereas BM07-59 had lost its motility. As shown in FIG. 3A, in LB or M1 medium with 70 mM fructose, the mutant exhibited the tendency to precipitate (autoagglutination). Autoagglutination in unshaken liquid medium is a common phenotype displayed by *rhizobia* with LPS defects. Therefore, BM07-59 was investigated for its LPS production. The LPS from the parental and mutant strain were extracted with proteinase K, resolved by SDS-PAGE, and silver stained. As shown in FIG. 3B, the extract obtained from the parental strain produced an LPS profile showing a low molecular weight (LMW) band and a series of high molecular weight (HMW) bands in a ladder-like pattern. Comparisons with known LPS profiles from *Pseudomonas* and other bacteria suggest that the LMW band corresponds to the rough LPS (lipid A plus core) and the HMW bands to the smooth LPS (complete LPS molecules with different number of attached O-antigen units). The mutant did not produce the smooth LPS bands and showed faint LMW LPS bands with different electrophoretic mobility from the parental bands as shown in FIG. 3B. The results indicated that the BM07-59 isolated by the present invention was damaged in the production of normal lipopolysaccharide.

UDP-glucose formed through the GalU catalyzed reaction can serve as glucose donor for core and O-antigen polysaccharide biosynthesis in the production of lipopolysaccharide. To determine why the O-antigen is missing in BM07-59, the composition of lipopolysaccharide was analyzed from wild-type and mutant strains grown in M1 medium containing 70 mM fructose at 30° C. Lipopolysaccharide purified from wild type and BM07-59 is predominantly composed of a lipid, with 10.7% and 3.5% of the lipopolysaccharide composed of carbohydrate, respectively. The carbohydrate fraction of lipopolysaccharide from wild-type strain contained rhamnose, xylose, mannose, glucose, N-acetyl glucosamine, and 3-deoxy-D-manno-oct-2-ulsonic acid (KDO) in a mole ratio of 31.8:1.7:0.3:50.2:14.9:1.1, respectively, whereas the carbohydrate fraction of lipopolysaccharide from BM07-59 contained rhamnose, glucose, N-acetyl glucosamine and KDO in a mole ratio of 3.9:11.2:30.8:54.1, respectively. Thus, in comparison with the wild-type lipopolysaccharide, the lipopolysaccharide from BM07-59 contained a much smaller molar amount of rhamnose and glucose but a much larger (50-fold) molar amount of KDO was detected in the mutant lipopolysaccharide. This significant difference in sugar composition of lipopolysaccharide between wild-type and mutant strains clearly reflects the fact that BM07-59 is unable to supply UDP-glucose for O-antigen and core lipopolysaccharide synthesis.

To further confirm that galU gene is involved in LPS and EBP production, a complementary assay was performed. Plasmid pBBR-KT galU harboring galU gene from *P. putida* KT2440 was introduced into BM07-59 to recover GalU activity. As expected, the mutant BM07-59 (KT GalU) complemented with *P. putida* KT2440 galU restored the parental phenotype for colony morphology (see FIG. 1A), EBP production (see 3 in FIG. 1B), and LPS synthesis (see 3 in FIG. 3B). These results indicated that the expression of galU gene from *P. putida* KT2440 in BM07-59 had compensated for the GalU function that BM07-59 lacked. The swimming motility was not fully restored to the parental level but was significantly increased in comparison with BM07-59.

Significant Increase in PHA Accumulation in BM07-59 Mutant

Figure 4A:
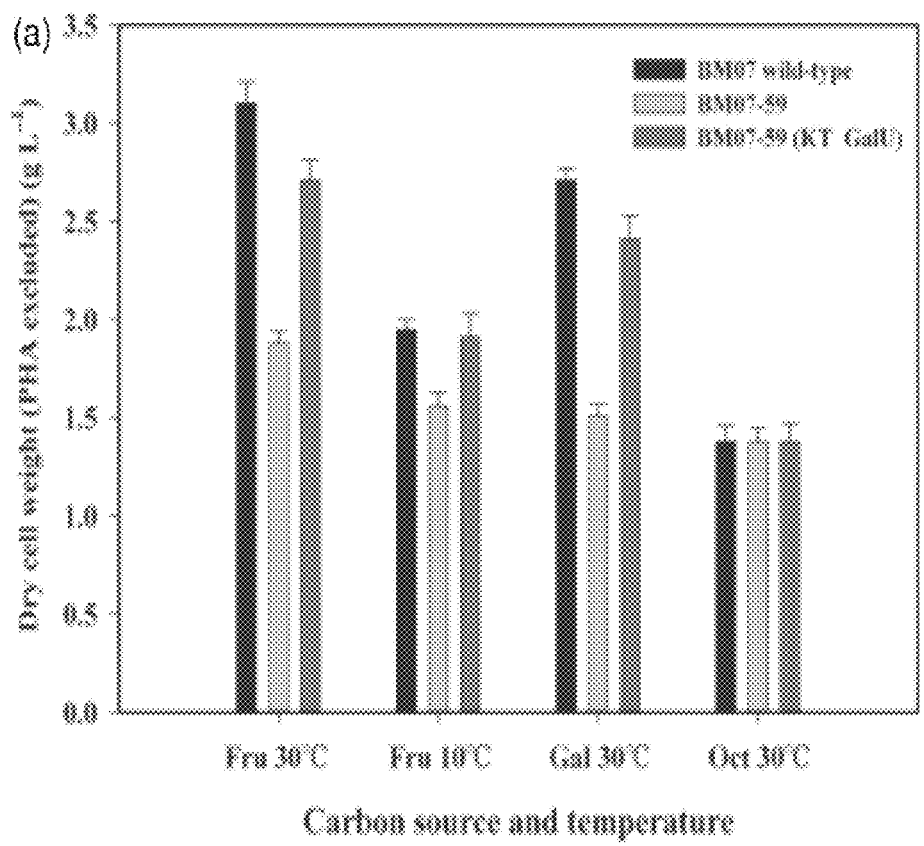
FIG. 4A shows the cell growth of BM07 wild type, BM07-59, and BM07-59 (KT GalU) grown on 70 mM fructose at 30° C. for 72 hours and 10° C. for 168 hours, 70 mM galactose at 30° C. for 96 hours, and 40 mM sodium octanoate at 30° C. for 84 hours.
Figure 4B:
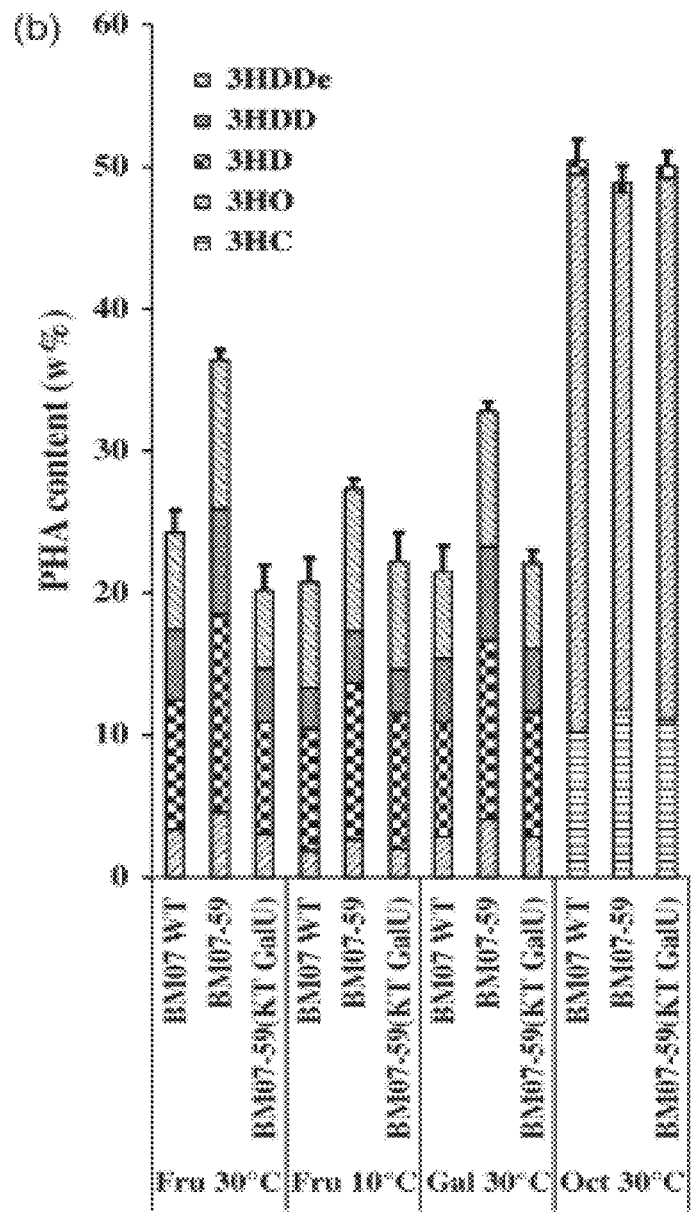
FIG. 4B shows the PHA accumulation of BM07 wild type, BM07-59, and BM07-59 (KT GalU) grown on 70 mM fructose at 30° C. for 72 hours and 10° C. for 168 hours, 70 mM galactose at 30° C. for 96 hours, and 40 mM sodium octanoate at 30° C. for 84 hours, in which Fru represents the fructose, Gal represents the galactose, Oct represents the sodium octanoate, 3HDDe represents the 3-hydroxy-cis-5-dodecanoate, 3HDD represents the 3-hydroxydodecanoate, 3HD represents the 3-hydroxydecanoate, 3HO represents the 3-hydroxyoctanoate, and 3HC represents the 3-hydroxyhexanoate.

An increase in the carbon-to-nitrogen (C/N) ratio is known to trigger exobiopolymer (EBP) and polyhydroxyalkanoate (PHA) synthesis. As shown in FIG. 4B, when BM07-59 was cultivated in M1 medium supplemented with 70 mM fructose and 1.0 g/L $(NH_4)_2SO_4$ as carbon and nitrogen sources at 30° C. and 10° C., the BM07-59 accumulated 36.4 and 27.4 wt % PHAs at 30° C. and 10° C., respectively, which is much higher than the 24.3 and 20.3 wt % PHAs produced by its parent BM07 wild type. However, as shown in FIG. 4A, the dry cell weight (DCW) of BM07-59 was 3.0 and 2.1 g/L at 30° C. and 10° C., respectively, which is lower than the 4.1 and 2.5 g/L of BM07 wild type. In *E. coli* and *A. hydrophile*, the galU mutants could not grow on galactose as sole carbon source. In contrast, BM07-59 was able to grow on galactose, exhibiting rather less cell growth but more PHA accumulation ability than BM07 wild type as shown in FIG. 4. The PHA composition produced by BM07-59 grown on fructose and galactose was similar to that by the wild type. The complementation of BM07-59 (KT GalU) resulted in a recovery of cell growth similar to the wild-type level and a reduction in PHA accumulation similar to the wild-type level. These results indicate that the carbon flux toward the synthesis of LPS or EBP could compete with the flux toward PHA accumulation. A similar mirror result was observed in *Pseudomonas putida* CA-3, of which the LPS overproducing mutant decreased the polyhydroxyalkanoates accumulation.

Figure 5:
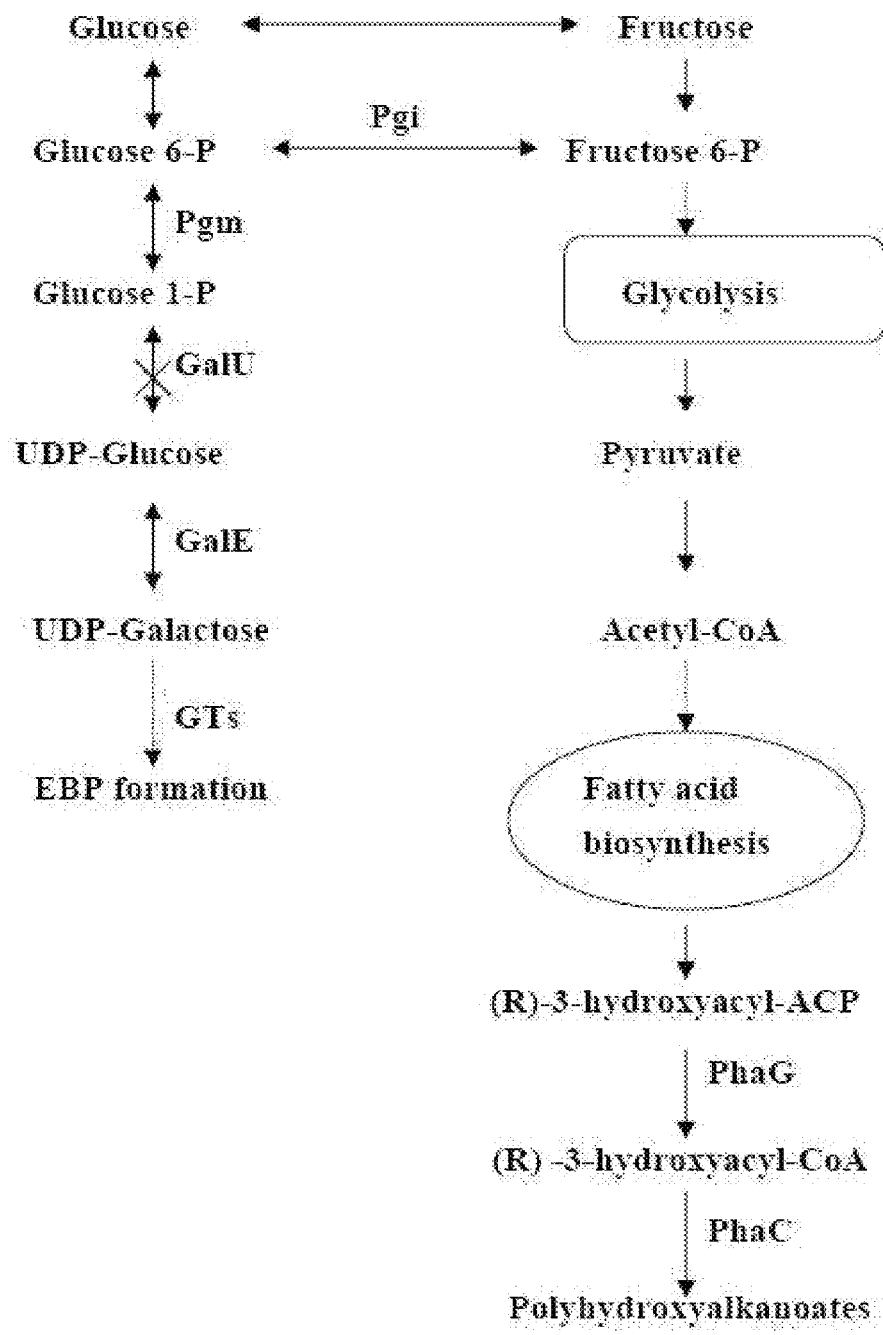
FIG. 5 shows the schematic representation of pathways according to the present invention and potential genes involved in the biosynthesis of PHA and EBP.

*P. fluorescens* BM07 was induced to excrete large amounts of EBP, composed of water-insoluble hydrophobic polypeptides and saccharides, by reducing the temperature to 10° C. or lower. The present invention aimed at finding the factors affecting EBP biosynthesis and PHA accumulation in *P. fluorescens* BM07. UDP-glucose pyrophosphorylase (GalU) appears to have an impact on EBP, LPS and PHA production in *P. fluorescens* BM07 as seen from the phenotypic characterization of BM07-59. Considering the increased PHA accumulation and deficit of O-antigen LPS and EBP synthesis in BM07-59 grown on fructose or galactose, the inventors suggest a simple model for the role of GalU in the synthesis of EBP and PHA in *P. fluorescens* BM07 as shown in FIG. 5. GalU is responsible for producing UDP-glucose from glucose 1-phosphate, which competes with fructose 6-phosphate for glucose 6-phosphate. Deletion of galU in BM07 blocks the formation of UDP-glucose, which is the main glucosyl donor for LPS and EBP synthesis, leading to a greater number of carbon resources available for PHA synthesis on fructose or galactose. PHA accumulation in the mutant from octanoate was similar to the level in the wild type despite lacking the O-antigen lipopolysaccharide of the mutant, suggesting the metabolic pathway for lipopolysaccharide might not be related to the PHA synthesis when the cells are grown on octanoate.

As described above, according to the present invention, the deletion of the gene associated with the production of the exobiopolymer (EBP) in the *Pseudomonas* strain redirects the carbon flux toward the production of the polyhydroxyalkanoic acid, thereby enhancing the production of the polyhydroxyalkanoic acid than the wild type.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An isolated *Pseudomonas fluorescens* mutant overproducing polyhydroxyalkanic acid (PHA), compared to a wild type *Pseudomonas fluorescens*, produced by disrupting a galU gene associated with the production of an exobiopolymer.

2. The mutant of claim 1, wherein the *Pseudomonas fluorescens* is *Pseudomonas fluorescens* BM07 (Accession no.: KCTC 10005BP).

* * * * *